(12) United States Patent
Cornish et al.

(10) Patent No.: US 7,575,866 B2
(45) Date of Patent: Aug. 18, 2009

(54) LIGAND/BINDING PARTNER BIO-LABELING SYSTEMS

(76) Inventors: Virginia Cornish, 450 Riverside Dr., Apt. 2, New York, NY (US) 10027; Michael Sheetz, 560 Riverside Dr., Apt. 7B, New York, NY (US) 10027; Larry Miller, 423 W. 120th St., Apt. 101, New York, NY (US) 10027

(*) Notice: Subject to any disclaimer, the term of this patent is extended or adjusted under 35 U.S.C. 154(b) by 166 days.

(21) Appl. No.: 11/219,506

(22) Filed: Sep. 1, 2005

(65) Prior Publication Data

US 2006/0211007 A1 Sep. 21, 2006

Related U.S. Application Data

(63) Continuation of application No. PCT/US2004/006156, filed on Mar. 2, 2004.

(60) Provisional application No. 60/451,595, filed on Mar. 3, 2003.

(51) Int. Cl.
*C12Q 1/68* (2006.01)
*C12Q 1/26* (2006.01)
*G01N 33/53* (2006.01)
*G01N 33/573* (2006.01)

(52) U.S. Cl. .................. 435/6; 435/7.1; 435/7.6; 435/7.71; 435/25

(58) Field of Classification Search ................ None
See application file for complete search history.

(56) References Cited

FOREIGN PATENT DOCUMENTS

| WO | WO/98/07844 | 2/1998 |
|---|---|---|
| WO | WO/00/23621 | 4/2000 |
| WO | WO/01/53355 | 7/2001 |
| WO | WO/01/88168 | 11/2001 |
| WO | WO/02/068678 | 9/2002 |
| WO | WO/2004/070351 | 8/2004 |

OTHER PUBLICATIONS

Lin et al, Supplementary Info/material for Linja9941532, J. Am. Chem. Soc., 2000, vol. 122: pp. S1-S12.*
Baccanari, D. et al., "Effect of a Single Amino Acid Substitution on *Escherichia coli* Dihydrofolate Reductase Catalysis and Ligand Binding", J. Biol. Chem. 1981: vol. 256: pp. 1738-1747.*
Kaufman, R. et al., "The Phosphorylation State of Eucaryotic Initiation Factor 2 Alters Translational Efficiency of Specific mRNAs", Mol. Cell. Biol., 1989, vol. 9: pp. 946-958.*
Keppler et al., 2004, Labeling of fusion proteins with synthetic fluorophores in live cells, Proc. Natl. Acad. Sci. USA, 101(27):9955-9959.
Milleret el., 2004, Methotrexate conjugates: a molecular in vivo protein tag, Angew Chem Int Ed Engl. 43(13):1672-5.
Ishibashi et al., 2003, IL-2 or IL-4 mRNA as a potential flow cytometric marker molecule for selective collection of living T helper 1 or T helper 2 lymphocytes, Anal. Chem., 75, 2715-2723.
Knemeyer et al., 2003, Detection and identification of single molecules in living cells using spectrally resolved fluorescence lifetime imaging microscopy, Anal. Chem., 75, 2147-2153.
Adams et al., 2002, New biarsenical ligands and tetracysteine motifs for protein labeling in vitro and in vivo: synthesis and biological applications, J. Am. Chem. Soc.124(21):6063-6076.
Bhaumik et al., 2002, Optical imaging of Renilla luciferase reporter gene expression in living mice, Proc. Natl. Acad. Sci. U.S.A. 99:377-382.
Campbell et al., 2002, A monomeric red fluorescent protein, Proc. Natl. Acad. Sci. U.S.A. 99(12):7877-7882.
Chan et al., 2002, Structural studies on bioactive compounds. Part 36: design, synthesis and biological evaluation of pyrimethamine-based antifolates against Pneumocystis carinii, Bioorg. Med/ Chem. 10(9):3001-3010.
Debnath, 2002, Pharmacophore mapping of a series of 2,4-diamino-5-deazapteridine inhibitors of Mycobacterium avium complex dihydrofolate reductase, J. Med. Chem. 45(1): 41-53.
Gilbert, 2002, Inhibitors of dihydrofolate reduces in Leishmania and trypanosomes Biochim Biophys Acta 1587(2-3):249-57.
Molina et al., 2002, A transformed fish cell line expressing a green fluorescent protein-luciferase fusion gene responding to cellular stress, Toxicol. In Vitro 16(2):201-207.
Lau et al., 2001, Efficacies of lipophilic inhibitors of dihydrofolate reductase against parasitic protozoa, Antimicrob. Agents Chemother. 45(1):187-95.
Nagakubo et al., 2001, Characteristics of transport of fluoresceinated methotrexate in rat small intestine, Life Sci. 69(7):739-747.
Ozawa et al., 2001, Split luciferase as an optical probe for detecting protein-protein interactions in mammalian cells based on protein splicing, Anal. Chem. 73(11):2516-2521.
Subramaniam et al., 2001, Direct visualization of protein interactions in plant cells, Nature Biotechnol. 19(8):769-772.
Suling and Maddry, 2001, Antimycobacterial activity of 1-deaza-7,8-dihydropteridine derivatives against Mycobacterium tuberculosis and Mycobacterium avium complex in vitro J. Antimicrob. Chemother, 47(4):451-454.
Wang et al., 2001, A Study of protein-protein interactions in living cells using luminescence resonance energy transfer (LRET) from Renilla luciferase to Aequorea GFP, Mol. Gen. Genet. 264(5):578-587.
Griffin et al., 2000, Fluorescent labeling of recombinant proteins in living cells with F1AsH, Methods Enzymol. 327:565-578.

(Continued)

*Primary Examiner*—Michael Burkhart
(74) *Attorney, Agent, or Firm*—Baker Botts LLP

(57) ABSTRACT

The present invention relates to methods and compositions which utilize binding relationships between detector molecules and their ligands for labeling molecules of interest in vivo. A "target" molecule is linked to a detector molecule (such as a protein or a nucleic acid) and the function and/or location of the target molecule is monitored by binding the detector molecule its ligand, which carries a detectable label. In particular embodiments of the invention, an intracellular fusion protein comprising a target protein and a detector protein is bound to a membrane-permeable, fluorescently-labeled ligand of the detector protein, thereby providing an adjunct or alternative to Green Fluorescent Protein.

3 Claims, 8 Drawing Sheets

OTHER PUBLICATIONS

Figure 2A:
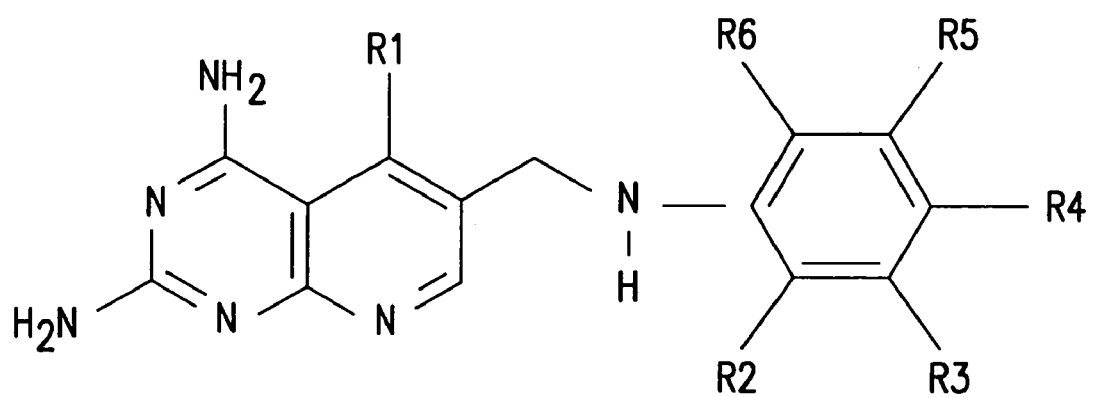

Lin et al., 2000, Dexamethasone-Methotrexate: An Efficient Chemical Inducer of Protein Dimerization In Vivo, J. Am. Chem. Soc. 122:4247-4248.

Suling et al., 2000, Antimycobacterial activities of 2,4-diamino-5-deazapteridine derivatives and effects on mycobacterial dihydrofolate reductase, Antimicrob. Agents Chemother. 44:2784-2793.

Famulok et al., 1999, Aptamers as tools in molecular biology and immunology, Curr Top Microbiol Immunol. 243:123-36.

Farinas and Verkman, 1999, Receptor-mediated targeting of fluorescent probes in living cells, J. Biol. Chem. 274:7603-7606.

Karp et al., 1999, A streptavidin-luciferase fusion protein: comparison and applications, Biomol. Eng. 16(1-4):101-104.

Clackson et al, 1998, Redesigning an FKBP-ligand interface to generate chemical dimerizers with novel specificity, Proc. Natl. Acad. Sci. U.S.A. 95:10437-10442.

Clackson, 1998, Redesigning small molecule-protein interfaces, Curr. Opin. Struct. Biol. 8:451-458.

Griffin et al., 1998, Specific covalent labeling of recombinant protein molecules inside live cells, Science 281: 269-272.

Amara et al., 1997, A versatile synthetic dimerizer for the regulation of protein-protein ineractions Proc. Natl. Acad. Sci. U.S.A. 94:10618-10623.

Jolivet et al., 1997, Confocal microscopy visualization of antifolate uptake by the reduced folate carrier in human leukaemic cells, Br J Cancer. 76(6):734-8.

Weiss et al., 1997, RNA aptamers specifically interact with the prion protein PrP J. Virol. 71(11):8790-8797.

Belshaw et al., 1996, Controlling protein association and subcellular localization with a synthetic ligand that induces heterodimerization of proteins, Proc. Natl. Acad. Sci. U.S.A. 93:4604-4607.

Carey et al., 1996, Evidence using a green fluorescent protein-glucocorticoid receptor chimera that the Ran/TC4 GTPase mediates an essential function independent of nuclear protein import, J. Cell Biol. 133(5):985-986.

Farrar et al., 1996, Activation of the Raf-1 kinase cascade by coumerycin-induced dimerization, Nature 383:178-181.

Heim et al., 1996, Engineering green fluorescent protein for improved brightness, longer wavelengths and fluorescence resonance energy transfer, Curr. Biol. 6:178-182.

Htun et al., 1996, Visualization of glucocorticoid receptor translocation and intranuclear organization in living cells with a green fluorescent protein chimera, Proc. Natl. Acad. Sci. U.S.A. 93(10):4845-4850.

Knowles et al., 1996, Translocation of RNA granules in living neurons, J. Neurosci. 16, 7812-7820.

Mitra et al., 1996, Fluorescence resonance energy transfer between blue-emitting and red-shifted excitation derivatives of the green fluorescent protein, Gene 173:13-17.

Ogawa et al., 1995, Localization, trafficking, and temperature-dependence of the Aequorea green fluorescent protein in cultured vertebrate cells, Proc. Natl. Acad. Sci. U.S.A. 92:11899-11903.

Banerjee et al., 1994, Transfection with a cDNA encoding a Ser31 or Ser34 mutant human dihydrofolate reductase into Chinese hamster ovary and mouse marrow progenitor cells confers methotrexate resistance, Gene 139(2): 269-274.

Spencer et al., 1993, Controlling signal transduction with synthetic ligands Science, 262:1019-1024.

Assaraf et al., 1992, Characterization of the coexisting multiple mechanisms of methotrexate resistance in mouse 3T6 R50 fibroblasts, J. Biol. Chem. 267:5776-5784.

Trippett et al., 1992, Defective transport as a mechanism of acquired resistance to methotrexate in patients with acute lymphocytoc leukemia, Blood 80:1158-1162.

Fan et al., 1991, Affinity labeling of folate transport proteins with the N-hydroxysuccinimide ester of the gamma-isomer of fluorescein-methotrexate, Biochemistry. 30(18):4573-4580.

Assaraf et al., 1989, A fluorescein-methotrexate-based flow cytometric bioassay for measurement of plasma methotrexate and trimetrexate levels, Anal. Biochem. 178:287-293.

Appleman et al., 1988, Kinetics of the formation and isomerization of methotrexate complexes of recombinant human dihydrofolate reductase J. Biol. Chem. 263:10304-10313.

Benkovic et al., 1988, Insights into enzyme function from studies on mutants of dihydrofolate reductase Science 239:1105-1110.

Kuyper et al., 1985, Receptor-based design of dihydrofolate reductase inhibitors: comparison of crystallographically determined enzyme binding with enzyme affinity in a series of carboxy-substituted trimethoprim analogues J. Med. Chem. 28: 303-311.

Urlaub et al., 1985, Use of fluorescence-activated cell sorter to isolate mutant mammalian cells deficient in an internal protein, dihydrofolate reductase, Somat. Cell Mol. Genet. 11(1):71-77.

Simonsend and Levinson, 1983, Isolation and expression of an altered mouse dihydrofolate reductase cDNA, Proc. Natl. Acad. Sci. U.S.A. 80(9):2495-2499.

Bolin et al., 1982, Crystal structures of *Escherichia coli* and *Lactobacillus casei* dihydrofolate reductase refined at 1.7 A resolution. I. General features and binding of methotrexate, J. Biol. Chem. 257:13650-13662.

Rosowsky et al., 1982, A new fluorescent dihydrofolate reductase probe for studies of methotrexate resistance, J. Biol.Chem. 257(23):14162-14167.

Henderson et al., 1980, A fluorescent derivative of methotrexate as an intracellular marker for dihydrofolate reductase in L1210 cells, Arch. Biochem. Biophys. 202(1):29-34.

Kaufman et al., 1978, Quantitation of dihydrofolate reductase in individual parental and methotrexate-resistant murine cells. Use of a fluorescence activated cell sorter, J. Biol. Chem. 253(16):5852-5860.

Abida et al; Receptor-Dependence of the Transcription Read-Out In A Small-Molecule Three-Hybrid System; Chembiochem: A European Journal of Chemical Biology; Sep. 2, 2002; vol. 3, No. 9, pp. 887-895.

Alam et al.; Reporter Genes: Application To The Study of Mammalian Gene Transcription; Analytical Biochemistry; Aug. 1, 1990; vol. 188, No. 2, pp. 245-254.

Asselbergs et al.; Use of the *Escherichia Coli* Chromosomal DHFR Gene As Selection Marker in Mammalian Cells; Journal of Biotechnology; Dec. 1, 1995; vol. 43, No. 2; pp. 133-138.

Bertrand et al.; Localization of ASH1 mRNA Particles in Living Yeast; Molecular Cell; Oct. 1998; vol. 2, No. 4; pp. 437-445.

Griffin et al.; Specific Covalent Labeling of Recombinant Protein Molecules Inside Live Cells; Amer. Assoc. For the Advancement of Science; Jul. 10, 1998; vol. 281; pp. 269-272.

Gu et al.; Effect of Amplification of DHFR and LAC Z Genes On Growth And Beta-Galactosidase Expression in Suspension Cultures of RecombinantCho Cells; Cytotechnology; 1992; vol. 9; pp. 237-245.

Gu et al.; Metabolic Burden in Recombinant CHO Cells: Effect of DHFR Gene Amplification and LacZ Expression; Cytotechnology; 1995; vol. 18, No. 3; pp. 159-166.

Hawkins et al.; Delivery of Radionuclides To Pretargeted Monoclonal Antibodies Using Dihydrofolate Reductase and Methodtrexate In An Affinity System; Amer. Assoc. For Cancer Research; May 15, 1993; vol. 53, No. 10; pp. 2368-2373.

Long et al.; Spatial Consequences of Defective Processing of Specific Yeast mRNAs Revealed By Fluorescent in Situ Hybridization; RNA; Dec. 1995; vol. 1, No. 10; pp. 1071-1078.

Michnick et al.; Detection of Protein Protein Interactions By Protein Fragment Complementation Strategies; Methods in Enzymology; vol. 328; 2000; pp. 208-230.

Moter et al.; Fluorescence In Situ Hybridization (FISH) For Direct Visualization of Microorganisms; Journal of Microbiological Methods; Jul. 2000; vol. 41, No. 2; pp. 85-112.

Remy et al; Visualization of Biochemical Networks in Living Cells; Proc. National Acad. of Sciences; Jul. 2001; vol. 98, No. 14; pp. 7678-7683.

Whitney et al; A Genome-Wide Functional Assay of Signal Transduction in Living Mammalian Cells; Nature Biotech; Dec. 1998; vol. 16, No. 13; pp. 1329-1333.

Wu et al.; Organelle PH Studies Using Targeted Avidin and Fluorescein-Biotin; Chem & Bio; Mar. 2000; vol. 7, No. 3; pp. 197-209.

Zhang et al.; Creating New Fluorescent Probes For Cell Biology; Dec. 2002; vol. 3, No. 12; pp. 906-918.

\* cited by examiner

*murine* DHFR

MVRPLNCIVAVSQNMGIGKNGDLPWPPLRNEFKYFQRMTTTSSVEGKQNLVIM
GRKTWFSIPEKNRPLKDRINIVLSRELKEPPRGAHFLAKSLDDALRLIEQPELASK
VDMVWIVGGSSVYQEAMNQPGHLRLFVTRIMQEFESDTFFPEIDLGKYKLLPEY
PGVLSEVQEEKGIKYKFEVYEKKD

FIG.1A

*human* DHFR

MVGSLNCIVAVSQNMGIGKNGDLPWPPLRNEFRYFQRMTTTSSVEGKQNLVIM
GKKTWFSIPEKNRPLKGRINLVLSRELKEPPQGAHFLSRSLDDALKLTEQPELAN
KVDMVWIVGGSSVYKEAMNHPGHLKLFVTRIMQDFESDTFFPEIDLEKYKLLPE
YPGVLSDVQEEKGIKYKFEVYEKND

FIG.1B

*Mycobacterium avium* DHFR

MTRAEVGLVWAQSTSGVIGRGGDIPWSVPEDLTRFKEVTMGHTVIMGRRTWES
LPAKVRPLPGRRNVVVSRRPDFVAEGARVAGSLEAALAYAGSDPAPWVIGGAQI
YLLALPHATRCEVTEIEIDLRRDDDDALAPALDDSWVGETGEWLASRSGLRYRF
HSYRRDPRSSVRGCSPSRPS

FIG.1C

*Drosophila melanogaster* DHFR

MLRFNLIVAVCENFGIGIRGDLPWRIKSELKYFSRTTKRTSDPTKQNAVVMGRKT
YFGVPESKRPLPDRLNIVLSTTLQESDLPKGVLLCPNLETAMKILEEQNEVENIWI
VGGSGVYEEAMASPRCHRLYITQIMQKFDCDTFFPAIPDSFREVAPDSDMPLGVQ
EENGIKFEYKILEKHS

FIG.1D

*Esherichia coli* DHFR

MKLSLMVAISKNGVIGNGPDIPWSAKGEQLLFKAITYNQWLLVGRKTFESMGAL
PNRKYAVVTRSSFTSDNENVLIFPSIKDALTNLKKITDHVIVSGGGEIYKSLIDQVD
TLHISTIDIEPEGDVYFPEIPSNFRPVFTQDFASNINYSYQIWQKG

FIG.1E

*Plasmodium falciparum* DHFR-TS

MMEQVCDVFDIYAICACCKVESKNEGKKNEVFNNYTFRGLGNKGVLPWKCNSL
DMKYFCAVTTYVNESKYEKLKYKRCKYLNKETVDNVNDMPNSKKLQNVVVM
GRTNWESIPKKFKPLSNRINVILSRTLKKEDFDEDVYIINKVEDLIVLLGKLNYYK
CFIIGGSVVYQEFLEKKLIKKIYFTRINSTYECDVFFPEINENEYQIISVSDVYTSNN
TTLDFIIYKKTNNKMLNEQNCIKGEEKNNDMPLKNDDKDTCHMKKLTEFYKNV
DKYKINYENDDDDEEEDDFVYFNFNKEKEEKNKNSIHPNDFQIYNSLKYKYHPE
YQYLNIIYDIMMNGNKQSDRTGVGVLSKFGYIMKFDLSQYFPLLTTKKLFLRGIIE
ELLWFIRGETNGNTLLNKNVRIWEANGTREFLDNRKLFHREVNDLGPIYGFQWR
HFGAEYTNMYDNYENKGVDQLKNIINLIKNDPTSRRILLCAWNVKDLDQMALPP
CHILCQFYVFDGKLSCIMYQRSCDLGLGVPFNIASYSIFTHMIAQVCNLQPAQFIH
VLGNAHVYNNHIDSLKIQLNRIPYPFPTLKLNPDIKNIEDFTISDFTIQNYVHHEKIS
MDMAA

FIG. 1F

Substitution at DMDP position | IC$_{50}$ (nM) for:

| Derivative no.[a] | SRI no.[c] | R1 | R2 | R3 | R4 | R5 | R6 | Human DHFR | MAC DHFR | Selectivity ratio |
|---|---|---|---|---|---|---|---|---|---|---|
| 1 | 8686 | -CH$_3$ | -OCH$_2$CH$_3$ | -H | -H | -OCH$_2$CH$_3$ | -H | 2,300 | 0.84 | 2,738 |
| 2 | 8117 | -CH$_3$ | -OCH$_3$ | -H | -H | -OCH$_3$ | -H | 1,000 | 1.1 | 909 |
| 3 | 8687[c] | -CH$_3$ | -OCH$_2$CH$_3$ | -H | -H | -OCH$_2$CH$_3$ | -H | 1,000 | 1.4 | 714 |
| 4 | 8202 | -CH$_3$ | -CH$_3$ | -H | -H | -OCH$_3$ | -H | 150 | 0.40 | 375 |
| 5 | 9734 | -CH$_3$ | -CH$_3$ | -H | -Br | -H | -CH$_3$ | 1,900 | 5.3 | 358 |
| 6 | 8922 | -CH$_2$CH$_3$ | -OCH$_3$ | -H | -H | -OCH$_3$ | -H | 1,000 | 2.8 | 357 |
| 7 | 8229 | -CH$_3$ | -OCH$_3$ | -H | -H | -CH$_3$ | -H | 300 | 0.86 | 349 |
| 8 | 9786 | -CH$_3$ | -OCH$_3$ | -H | -H | -H | -H | 277 | 0.87 | 318 |
| 9 | 9674 | -CH$_3$ | -OCHF$_2$ | -H | -H | -CH$_3$ | -H | 250 | 1.1 | 227 |
| 10 | 9717 | -CH$_3$ | -F | -H | -H | -H | -CH$_3$ | 850 | 3.8 | 224 |
| 11 | 9643 | -CH$_3$ | -Cl | -H | -H | -CH$_3$ | -H | 120 | 0.91 | 132 |
| 12 | 8911 | -CH$_2$CH$_3$ | -Cl | -H | -H | -H | -H | 370 | 3.1 | 119 |
| 13 | 9672 | -CH$_3$ | -OCH$_3$ | -H | -CH$_3$ | -CH$_3$ | -H | 69 | 0.90 | 77 |
| 14 | 9826 | -CH$_3$ | -F | -H | -H | -F | -H | 68 | 0.91 | 75 |
| 15 | 9018 | -CH$_3$ | -OCH$_3$ | -H | -H | -H | -H | 57 | 0.92 | 62 |
| 16 | 9647 | -CH$_3$ | -CH$_3$ | -H | -C$_6$H$_5$ | -H | -H | 44 | 0.95 | 46 |
| 17 | 9782 | -CH$_3$ | -Cl | -H | -H | -CH$_3$ | -H | 33 | 0.78 | 42.3 |
| 18 | 9645[c] | -CH$_3$ | -Cl | -H | -F | -CH$_3$ | -H | 27 | 0.84 | 32.1 |
| 19 | 8574[c] | -CH$_3$ | -H | -H | -Cl | -H | -H | 36 | 1.2 | 30 |
| 20 | 8709 | -CH$_3$ | -OCH$_3$ | -OCH$_3$ | -H | -CF$_3$ | -H | 15 | 0.64 | 23.4 |
| 21 | 9675 | -CH$_3$ | -H | -H | -H | -OCH$_3$ | -H | 19 | 0.85 | 22 |
| 22 | 9644 | -CH$_3$ | -H | -Cl | -H | -F | -H | 17 | 0.82 | 20.7 |
| 23 | 9787 | -CH$_3$ | -H | -H | -OCHF$_2$ | -H | -H | 20 | 1.1 | 18 |

FIG. 2B

| No. | Cmpd | R1 | R2 | R3 | R4 | R5 | Val1 | Val2 | Val3 |
|---|---|---|---|---|---|---|---|---|---|
| 24 | 9981 | -CH$_3$ | -H | -OCH$_3$ | -OCH$_2$CH$_3$ | -H | 18 | 1.1 | 16.5 |
| 25 | 9980 | -CH$_3$ | -H | -OCH$_3$ | -OCH$_3$O(CH$_2$)$_2$CH$_3$ | -H | 15 | 0.93 | 16.1 |
| 26 | 7746 | -H | -H | -OCH$_3$ | -OCH$_3$ | -H | 3,900 | 240 | 16 |
| 27 | 9827 | -CH$_3$ | -H | -F | -OCH$_3$ | -H | 14 | 0.91 | 15 |
| 28 | 9596 | -CH$_3$ | -CH$_3$ | -H | -Cl | -H | 2.8 | 0.19 | 14.7 |
| 29 | 8758 | -CH$_2$OCH$_3$ | -OCH$_3$ | -H | -H | -H | 31,000 | 2,400 | 12.9 |
| 30 | 8710$^c$ | -CH$_3$ | -H | -OCH$_3$ | -OCH$_3$ | -H | 8.7 | 0.73 | 11.9 |
| 31 | 9733 | -CH$_3$ | -OCH$_3$ | -H | -OCH$_3$ | -H | 10 | 0.94 | 10.6 |
| 32 | 8577 | -H | -H | -H | -CH$_3$ | -H | 670 | 73 | 9.2 |
| 33 | 9646 | -CH$_3$ | -H | -H | -H | -H | 8.0 | 0.89 | 9.0 |
| 34 | 9595 | -CH$_3$ | -Cl | -Cl | -Cl | -H | 6.1 | 0.79 | 7.7 |
| 35 | 9600 | -CH$_3$ | -CH$_3$ | -Cl | -Cl | -H | 6.7 | 0.90 | 7.44 |
| 36 | 8692 | -CH$_3$ | -H | -OCH$_3$ | -H | -H | 5.1 | 0.70 | 7.29 |
| 37 | 9614 | -CH$_3$ | -H | -CH$_3$ | -H | -H | 6.1 | 0.87 | 7.01 |
| 38 | 9613 | -CH$_3$ | -CH$_3$ | -H | -CH$_3$ | -H | 5.9 | 0.85 | 6.94 |
| 39 | 9676 | -CH$_3$ | -Br | -H | -Br | -Br | 4.6 | 0.70 | 6.6 |
| 40 | 9599 | -CH$_3$ | -CH$_3$ | -H | -Br | -H | 5.2 | 0.82 | 6.34 |
| 41 | 9612 | -CH$_3$ | -H | -Br | -H | -H | 3.7 | 0.60 | 6.17 |
| 42 | 8227 | -CH$_3$ | -H | -H | -CH | -CF$_3$ | 5.5 | 0.93 | 5.91 |
| 43 | 7714 | -CH$_3$ | -H | -Cl | -H | -OCH$_3$ | 4.7 | 0.82 | 5.7 |
| 44 | 9632 | -CH$_3$ | -H | -Br | -OC | -H | 5.0 | 0.92 | 5.43 |
| 45 | 8766 | -CH$_2$OCH$_3$ | -F | -OCH$_3$ | -Cl | -H | 6,100 | 1,200 | 5.1 |
| 46 | 9684 | -CH$_3$ | -OCH$_3$ | -OCH$_3$ | -OCH$_3$ | -H | 4.1 | 0.86 | 4.8 |
| 47 | 8228 | -CH$_3$ | -OCH$_3$ | -OCH$_3$ | -H | -H | 2.7 | 0.66 | 4.1 |
| 48 | 8923 | -CH$_2$CH$_3$ | -H | -Cl | -CF$_3$ | -H | 3.6 | 0.88 | 4.1 |
| 49 | 9683 | -CH$_3$ | -H | -Br | -CF$_3$ | -H | 3.2 | 0.82 | 3.9 |
| 50 | 8765 | -CH$_2$OCH$_3$ | -OCH$_3$ | -H | -OCH$_3$ | -H | 1,300 | 550 | 2.4 |
| 51 | 8759 | -CH$_2$OCH$_3$ | -H | -H | -Cl | -H | 2,600 | 1,500 | 1.76 |

FIG. 2C

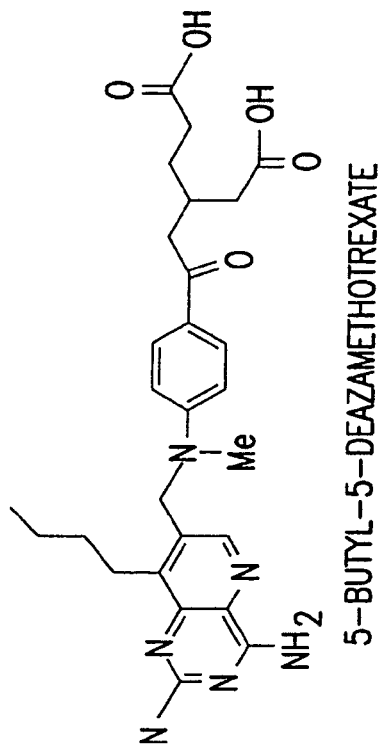
FIG. 5B  5-BUTYL-5-DEAZAMETHOTREXATE
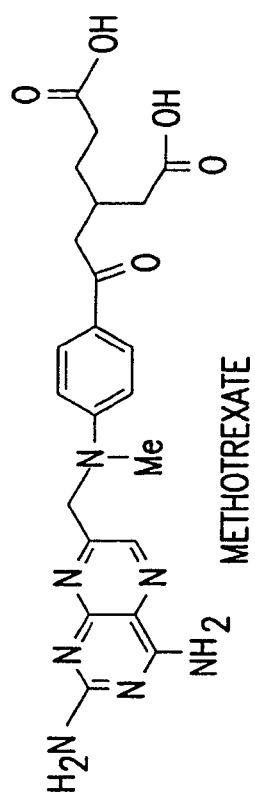
FIG. 5A  METHOTREXATE

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Gly Cys Val Gln Cys Lys Asp Lys Glu Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Gly Cys Ile Lys Ser Lys Glu Asn Lys Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 3

Gly Cys Thr Leu Ser Ala Glu Glu Arg Ala
1               5                   10

<210> SEQ ID NO 4
<211> LENGTH: 187
<212> TYPE: PRT
<213> ORGANISM: Mus musculus

<400> SEQUENCE: 4
```

```
Met Val Arg Pro Leu Asn Cys Ile Val Ala Val Ser Gln Asn Met Gly
 1               5                  10                  15

Ile Gly Lys Asn Gly Asp Leu Pro Trp Pro Leu Arg Asn Glu Phe
             20                  25                  30

Lys Tyr Phe Gln Arg Met Thr Thr Thr Ser Ser Val Glu Gly Lys Gln
             35                  40                  45

Asn Leu Val Ile Met Gly Arg Lys Thr Trp Phe Ser Ile Pro Glu Lys
 50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
             85                  90                  95

Ala Leu Arg Leu Ile Glu Gln Pro Glu Leu Ala Ser Lys Val Asp Met
             100                 105                 110

Val Trp Ile Val Gly Gly Ser Ser Val Tyr Gln Glu Ala Met Asn Gln
             115                 120                 125

Pro Gly His Leu Arg Leu Phe Val Thr Arg Ile Met Gln Glu Phe Glu
 130                 135                 140

Ser Asp Thr Phe Phe Pro Glu Ile Asp Leu Gly Lys Tyr Lys Leu Leu
145                  150                 155                 160

Pro Glu Tyr Pro Gly Val Leu Ser Glu Val Gln Glu Glu Lys Gly Ile
             165                 170                 175

Lys Tyr Lys Phe Glu Val Tyr Glu Lys Lys Asp
             180                 185
```

<210> SEQ ID NO 5
<211> LENGTH: 187
<212> TYPE: PRT
<213> ORGANISM: Homo sapiens

<400> SEQUENCE: 5

```
Met Val Gly Ser Leu Asn Cys Ile Val Ala Val Ser Gln Asn Met Gly
 1               5                  10                  15

Ile Gly Lys Asn Gly Asp Leu Pro Trp Pro Leu Arg Asn Glu Phe
             20                  25                  30

Arg Tyr Phe Gln Arg Met Thr Thr Thr Ser Ser Val Glu Gly Lys Gln
             35                  40                  45

Asn Leu Val Ile Met Gly Lys Lys Thr Trp Phe Ser Ile Pro Glu Lys
 50                  55                  60

Asn Arg Pro Leu Lys Gly Arg Ile Asn Leu Val Leu Ser Arg Glu Leu
 65                  70                  75                  80

Lys Glu Pro Pro Gln Gly Ala His Phe Leu Ser Arg Ser Leu Asp Asp
             85                  90                  95

Ala Leu Lys Leu Thr Glu Gln Pro Glu Leu Ala Asn Lys Val Asp Met
             100                 105                 110

Val Trp Ile Val Gly Gly Ser Ser Val Tyr Lys Glu Ala Met Asn His
             115                 120                 125

Pro Gly His Leu Lys Leu Phe Val Thr Arg Ile Met Gln Asp Phe Glu
 130                 135                 140

Ser Asp Thr Phe Phe Pro Glu Ile Asp Leu Glu Lys Tyr Lys Leu Leu
145                  150                 155                 160

Pro Glu Tyr Pro Gly Val Leu Ser Asp Val Gln Glu Glu Lys Gly Ile
             165                 170                 175

Lys Tyr Lys Phe Glu Val Tyr Glu Lys Asn Asp
             180                 185
```

<210> SEQ ID NO 6
<211> LENGTH: 181
<212> TYPE: PRT
<213> ORGANISM: Mycobacterium avium

<400> SEQUENCE: 6

Met Thr Arg Ala Glu Val Gly Leu Val Trp Ala Gln Ser Thr Ser Gly
1               5                   10                  15
Val Ile Gly Arg Gly Gly Asp Ile Pro Trp Ser Val Pro Glu Asp Leu
            20                  25                  30
Thr Arg Phe Lys Glu Val Thr Met Gly His Thr Val Ile Met Gly Arg
        35                  40                  45
Arg Thr Trp Glu Ser Leu Pro Ala Lys Val Arg Pro Leu Pro Gly Arg
    50                  55                  60
Arg Asn Val Val Ser Arg Arg Pro Asp Phe Val Ala Glu Gly Ala
65                  70                  75                  80
Arg Val Ala Gly Ser Leu Glu Ala Ala Leu Ala Tyr Ala Gly Ser Asp
                85                  90                  95
Pro Ala Pro Trp Val Ile Gly Gly Ala Gln Ile Tyr Leu Leu Ala Leu
            100                 105                 110
Pro His Ala Thr Arg Cys Glu Val Thr Glu Ile Glu Ile Asp Leu Arg
        115                 120                 125
Arg Asp Asp Asp Asp Ala Leu Ala Pro Ala Leu Asp Asp Ser Trp Val
    130                 135                 140
Gly Glu Thr Gly Glu Trp Leu Ala Ser Arg Ser Gly Leu Arg Tyr Arg
145                 150                 155                 160
Phe His Ser Tyr Arg Arg Asp Pro Arg Ser Ser Val Arg Gly Cys Ser
                165                 170                 175
Pro Ser Arg Pro Ser
            180

<210> SEQ ID NO 7
<211> LENGTH: 182
<212> TYPE: PRT
<213> ORGANISM: Drosophila melanogaster

<400> SEQUENCE: 7

Met Leu Arg Phe Asn Leu Ile Val Ala Val Cys Glu Asn Phe Gly Ile
1               5                   10                  15
Gly Ile Arg Gly Asp Leu Pro Trp Arg Ile Lys Ser Glu Leu Lys Tyr
            20                  25                  30
Phe Ser Arg Thr Thr Lys Arg Thr Ser Asp Pro Thr Lys Gln Asn Ala
        35                  40                  45
Val Val Met Gly Arg Lys Thr Tyr Phe Gly Val Pro Glu Ser Lys Arg
    50                  55                  60
Pro Leu Pro Asp Arg Leu Asn Ile Val Leu Ser Thr Thr Leu Gln Glu
65                  70                  75                  80
Ser Asp Leu Pro Lys Gly Val Leu Leu Cys Pro Asn Leu Glu Thr Ala
                85                  90                  95
Met Lys Ile Leu Glu Glu Gln Asn Glu Val Glu Asn Ile Trp Ile Val
            100                 105                 110
Gly Gly Ser Gly Val Tyr Glu Glu Ala Met Ala Ser Pro Arg Cys His
        115                 120                 125
Arg Leu Tyr Ile Thr Gln Ile Met Gln Lys Phe Asp Cys Asp Thr Phe

```
            130                 135                 140
Phe Pro Ala Ile Pro Asp Ser Phe Arg Glu Val Ala Pro Asp Ser Asp
145                 150                 155                 160

Met Pro Leu Gly Val Gln Glu Asn Gly Ile Lys Phe Glu Tyr Lys
                165                 170                 175

Ile Leu Glu Lys His Ser
            180

<210> SEQ ID NO 8
<211> LENGTH: 157
<212> TYPE: PRT
<213> ORGANISM: Escherichia coli

<400> SEQUENCE: 8

Met Lys Leu Ser Leu Met Val Ala Ile Ser Lys Asn Gly Val Ile Gly
1               5                   10                  15

Asn Gly Pro Asp Ile Pro Trp Ser Ala Lys Gly Glu Gln Leu Leu Phe
            20                  25                  30

Lys Ala Ile Thr Tyr Asn Gln Trp Leu Leu Val Gly Arg Lys Thr Phe
        35                  40                  45

Glu Ser Met Gly Ala Leu Pro Asn Arg Lys Tyr Ala Val Val Thr Arg
    50                  55                  60

Ser Ser Phe Thr Ser Asp Asn Glu Asn Val Leu Ile Phe Pro Ser Ile
65                  70                  75                  80

Lys Asp Ala Leu Thr Asn Leu Lys Lys Ile Thr Asp His Val Ile Val
                85                  90                  95

Ser Gly Gly Gly Glu Ile Tyr Lys Ser Leu Ile Asp Gln Val Asp Thr
            100                 105                 110

Leu His Ile Ser Thr Ile Asp Ile Glu Pro Glu Gly Asp Val Tyr Phe
        115                 120                 125

Pro Glu Ile Pro Ser Asn Phe Arg Pro Val Phe Thr Gln Asp Phe Ala
    130                 135                 140

Ser Asn Ile Asn Tyr Ser Tyr Gln Ile Trp Gln Lys Gly
145                 150                 155

<210> SEQ ID NO 9
<211> LENGTH: 608
<212> TYPE: PRT
<213> ORGANISM: Plasmodium falciparum

<400> SEQUENCE: 9

Met Met Glu Gln Val Cys Asp Val Phe Asp Ile Tyr Ala Ile Cys Ala
1               5                   10                  15

Cys Cys Lys Val Glu Ser Lys Asn Glu Gly Lys Lys Asn Glu Val Phe
            20                  25                  30

Asn Asn Tyr Thr Phe Arg Gly Leu Gly Asn Lys Gly Val Leu Pro Trp
        35                  40                  45

Lys Cys Asn Ser Leu Asp Met Lys Tyr Phe Cys Ala Val Thr Thr Tyr
    50                  55                  60

Val Asn Glu Ser Lys Tyr Glu Lys Leu Lys Tyr Lys Arg Cys Lys Tyr
65                  70                  75                  80

Leu Asn Lys Glu Thr Val Asp Asn Val Asn Asp Met Pro Asn Ser Lys
                85                  90                  95

Lys Leu Gln Asn Val Val Val Met Gly Arg Thr Asn Trp Glu Ser Ile
            100                 105                 110

Pro Lys Lys Phe Lys Pro Leu Ser Asn Arg Ile Asn Val Ile Leu Ser
```

-continued

```
            115                 120                 125
Arg Thr Leu Lys Lys Glu Asp Phe Asp Glu Asp Val Tyr Ile Ile Asn
    130                 135                 140
Lys Val Glu Asp Leu Ile Val Leu Leu Gly Lys Leu Asn Tyr Tyr Lys
145                 150                 155                 160
Cys Phe Ile Ile Gly Gly Ser Val Val Tyr Gln Glu Phe Leu Glu Lys
                165                 170                 175
Lys Leu Ile Lys Lys Ile Tyr Phe Thr Arg Ile Asn Ser Thr Tyr Glu
                180                 185                 190
Cys Asp Val Phe Phe Pro Glu Ile Asn Glu Asn Glu Tyr Gln Ile Ile
            195                 200                 205
Ser Val Ser Asp Val Tyr Thr Ser Asn Asn Thr Thr Leu Asp Phe Ile
    210                 215                 220
Ile Tyr Lys Lys Thr Asn Asn Lys Met Leu Asn Glu Gln Asn Cys Ile
225                 230                 235                 240
Lys Gly Glu Glu Lys Asn Asn Asp Met Pro Leu Lys Asn Asp Asp Lys
                245                 250                 255
Asp Thr Cys His Met Lys Lys Leu Thr Glu Phe Tyr Lys Asn Val Asp
                260                 265                 270
Lys Tyr Lys Ile Asn Tyr Glu Asn Asp Asp Asp Glu Glu Glu Asp
            275                 280                 285
Asp Phe Val Tyr Phe Asn Phe Asn Lys Glu Lys Glu Glu Lys Asn Lys
    290                 295                 300
Asn Ser Ile His Pro Asn Asp Phe Gln Ile Tyr Asn Ser Leu Lys Tyr
305                 310                 315                 320
Lys Tyr His Pro Glu Tyr Gln Tyr Leu Asn Ile Ile Tyr Asp Ile Met
                325                 330                 335
Met Asn Gly Asn Lys Gln Ser Asp Arg Thr Gly Val Gly Val Leu Ser
                340                 345                 350
Lys Phe Gly Tyr Ile Met Lys Phe Asp Leu Ser Gln Tyr Phe Pro Leu
            355                 360                 365
Leu Thr Thr Lys Lys Leu Phe Leu Arg Gly Ile Ile Glu Glu Leu Leu
    370                 375                 380
Trp Phe Ile Arg Gly Glu Thr Asn Gly Asn Thr Leu Leu Asn Lys Asn
385                 390                 395                 400
Val Arg Ile Trp Glu Ala Asn Gly Thr Arg Glu Phe Leu Asp Asn Arg
                405                 410                 415
Lys Leu Phe His Arg Glu Val Asn Asp Leu Gly Pro Ile Tyr Gly Phe
                420                 425                 430
Gln Trp Arg His Phe Gly Ala Glu Tyr Thr Asn Met Tyr Asp Asn Tyr
            435                 440                 445
Glu Asn Lys Gly Val Asp Gln Leu Lys Asn Ile Ile Asn Leu Ile Lys
    450                 455                 460
Asn Asp Pro Thr Ser Arg Arg Ile Leu Leu Cys Ala Trp Asn Val Lys
465                 470                 475                 480
Asp Leu Asp Gln Met Ala Leu Pro Pro Cys His Ile Leu Cys Gln Phe
                485                 490                 495
Tyr Val Phe Asp Gly Lys Leu Ser Cys Ile Met Tyr Gln Arg Ser Cys
                500                 505                 510
Asp Leu Gly Leu Gly Val Pro Phe Asn Ile Ala Ser Tyr Ser Ile Phe
            515                 520                 525
Thr His Met Ile Ala Gln Val Cys Asn Leu Gln Pro Ala Gln Phe Ile
    530                 535                 540
```

```
His Val Leu Gly Asn Ala His Val Tyr Asn Asn His Ile Asp Ser Leu
545                 550                 555                 560

Lys Ile Gln Leu Asn Arg Ile Pro Tyr Pro Phe Pro Thr Leu Lys Leu
                565                 570                 575

Asn Pro Asp Ile Lys Asn Ile Glu Asp Phe Thr Ile Ser Asp Phe Thr
            580                 585                 590

Ile Gln Asn Tyr Val His His Glu Lys Ile Ser Met Asp Met Ala Ala
        595                 600                 605

<210> SEQ ID NO 10
<211> LENGTH: 6
<212> TYPE: PRT
<213> ORGANISM: Artificial Sequence
<220> FEATURE:
<223> OTHER INFORMATION: Unsure
<220> FEATURE:
<221> NAME/KEY: VARIANT
<222> LOCATION: 3, 4
<223> OTHER INFORMATION: Xaa = Any Amino Acid

<400> SEQUENCE: 10

Cys Cys Xaa Xaa Cys Cys
 1               5
```

US 7,575,866 B2

LIGAND/BINDING PARTNER BIO-LABELING SYSTEMS

CROSS REFERENCE TO RELATED APPLICATION(S)

The present application is a continuation of International Patent Application No. PCT/US2004/006156, filed Mar. 2, 2004, published in English on Sep. 16, 2004 as International Patent Publication No. WO2004/078594, which claims priority to U.S. Provisional Application No. 60/451,595, filed Mar. 3, 2003, all of which are incorporated by reference herein in their entireties.

1. INTRODUCTION

The present invention relates to methods and compositions for detecting the location and/or function of a target molecule whereby the target molecule is linked, directly or indirectly via a detector molecule, to a labeled ligand. In particular embodiments of the invention, an intracellular fusion protein comprising a target protein and a detector protein is bound to a membrane-permeable, fluorescently-labeled ligand of the detector protein, thereby providing an adjunct or alternative to Green Fluorescent Protein.

2. BACKGROUND OF THE INVENTION

Genomics has identified a wealth of genes, but the function of most of these genes remains elusive. Technology does not yet provide straightforward methods for determining the biological role played by newly identified proteins.

2.1 Reporters of Promoter Activity

To understand a protein's function, it is helpful to define its expression pattern, for example, by determining the times and circumstances when transcription of the gene encoding the protein are elevated or depressed. One method of studying transcriptional activity is to link the promoter of the gene being studied to a "reporter" gene. One example of a well-known reporter gene commonly used in animal systems is the gene encoding beta-galactosidase. This enzyme can lyse a variety of substrates to yield, in a short period of time, detectable cleavage products (e.g. Galacto-Star™ chemiluminescent substrate sold by Applied Biosystems, Foster City, Calif.).

In plants, an example of a widely used reporter gene is beta-glucuronidase ("GUS"), which can cleave diverse substrates to generate products which are easily detectable (e.g. a chromogenic or non-fluorescent substrate can be cleaved to generate a colored or fluorescent product; Jefferson et al., 1987, EMBO J. 6:3901-3907; Jefferson, 1987, Plant Mol. Biol. Rep. 5:387-405). The assay for determining GUS activity is performed in vitro, requiring destruction of the promoter/GUS containing cell. Another drawback is that certain organisms produce their own beta glucuronidase enzyme, potentially causing a background problem.

Luciferase, an enzyme used by a number of organisms, including fireflies, to generate bioluminescence in the presence of specific substrates, can function as a sensitive reporter gene for promoter activity in vivo (Bhaumik and Gambhir, 2002, Proc. Natl. Acad. Sci. U.S.A. 99:377-382, published online Dec. 18, 2001), but has the disadvantages of being somewhat toxic and requiring special equipment to detect its bioluminescence.

Green Fluorescent Protein ("GFP") is a third type of reporter gene which offers the advantage of being intrinsically fluorescent, so that no extrinsic substrate need be supplied. The signal produced is easily detectable with commonly available laboratory equipment. Discovered by Shimomura et al. (1962, J. Cell. Comp. Physiol. 59:223-239) as a companion protein to the chemiluminescent protein aequorin in *Aequorea* jellyfish, GFP was cloned, years later, by Prasher et al. (1992, Gene 111:229-233). Subsequently, Chalfie et al. (1994, Science 263:802-805) and Inouye and Tsuji (1994, FEBS Lett. 341:277-280) demonstrated that the protein could fluoresce in organisms other than jellyfish. It thereafter became "one of the most widely studied and exploited proteins in biochemistry and cell biology" (Tsien, 1998, Annu. Rev. Biochem. 67:509-544, a comprehensive review on the subject). A disadvantage of GFP is its relatively low sensitivity, requiring a strong promoter to generate enough GFP for detection (Tsien, supra, at p. 532).

2.2 Fusion Tags

To appreciate the function of a protein, it is also usually necessary to study its relationships with subcellular structures and its participation in molecular pathways. While in vitro recreations of these interactions is possible, the most direct experiments probe the activities of the protein within its natural context, in a living cell.

Where the relevant interactions of a protein occur only at the surface of a cell, such studies can be performed using labeled antibodies that specifically bind to the protein. However, where, as is more often the case, intracellular relationships are important, the available methods are more limited. Many of the older techniques, such as immunohistochemical labeling, required that the cell be killed, fixed and sectioned.

Both luciferase (Karp and Oker-Blom, 1999, Biomol. Eng. 16(1-4):101-104) and GFP (see Tsien, supra) have been used in fusions with proteins of interest to provide information on localization and interactions with other molecules and subcellular structures, and fusions between GFP and luciferase have been prepared (for use in identifying cellular stressors; Molina et al., 2002, Toxicol. In Vitro 16(2):201-207). The luciferase protein has been split, one part fused to a first protein and the other fused to a second protein; and binding between the two proteins has been detected by reconstitution of luciferase activity (Ozawa et al., 2001, Anal. Chem. 73(11):2516-2521).

Moreover, luciferase and GFP, separately and in combination, have been used in energy transfer studies that can detect the spatial relationships between energy donor and energy acceptor molecules. For example, protein-protein interactions have been detected by luminescence energy transfer ("LRET") from *Renilla* luciferase to *Aequorea* GFP which occurs when a first protein linked, as a fusion protein, to luciferase binds to a second protein linked to GFP (Wang et al., 2001, Mol. Gen. Genet. 264(5):578-587). GFPs of different colors may be used to effect fluorescence resonance energy transfer ("FRET"; Tsien, supra at 534; Helm and Tsien, 1996, Curr. Biol. 6:178-182; Mitra et al., 1996, Gene 173:13-17).

The fusion proteins comprising luciferase and GFP have the same advantages and shortcomings of the individual proteins. Luciferase fusion proteins require the presence of particular substrates and specialized detection equipment. GFP, while requiring no substrate, produces a relatively weak signal and is only detectable at higher concentrations.

In addition, for dissecting the elements of multiple component systems, it would be advantageous to distinctively label the various elements. Each element of a pathway could, in theory, be fused to a fluorescent protein that could be distinguished by its fluorescence absorption and emission spectra. A limitation of the GFP system is that the variety of spectra available is limited. Efforts have been made to develop a red fluorescent protein (Campbell et al., 2002, Proc. Natl. Acad. Sci. U.S.A. 99(12):7877-7882). However, there remains a substantial need for a variety of labels sufficient to address the complexity of interactions being studied.

2.3 Prior Uses of Small Molecule Ligands

Labeled small molecule ligands have been used in the art to detect the presence of their binding partners. For example, fluorescently labeled methotrexate ("fMTX") has been used to identify cells deficient in its binding protein, dihydrofolate reductase ("DHFR"; Urlaub et al., 1985, Somat. Cell Mol. Genet. 11(1):71-77; Henderson et al., 1980, Arch. Biochem. Biophys. 202(1):29-34; Kaufman et al., 1978, J. Biol. Chem. 253(16):5852-5860). Because methotrexate is toxic to rapidly dividing cells and, as such, is used as chemotherapy for certain cancers, fMTX has been used to assess drug uptake by cancer cells (e.g., to predict therapeutic response; Jolivet et al., 1997, Int. J. Cancer 76(6):734-738), to study the mechanisms of drug resistance (Assaraf et al., 1992, J. Biol. Chem. 267:5776-5784; Trippett et al., 1992, Blood 80:1158-1162) and toxic side-effects (Nagakubo et al., 2001, Life Sci. 69(7): 739-747) and to measure plasma levels of MTX (Assaref et al., 1989, Anal. Biochem. 178:287-293).

fMTX has been used to determine the intracellular location of a fusion protein ("DHFR/GR") comprising murine DHFR and a portion of the glucocorticoid receptor protein (Israel and Kaufman, 1993, Proc. Natl. Acad. Sci. U.S.A. 90:4290-4294). In these studies, addition of either the glucocorticoid agonist, dexamethasone, or the antagonist, RU486, resulted in the translocation of the DHFR/GR into the nucleus, as demonstrated by binding to fMTX and visualization by fluorescence microscopy. Subsequent studies replaced DHFR with GFP for fusion with glucocorticoid receptor protein (Carey et al., 1996, J. Cell Biol. 133(5):985-986; Ogawa et al., 1995, Proc. Natl. Acad. Sci. U.S.A. 92:11899-11903; Htun et al., 1996, Proc. Natl. Acad. Sci. U.S.A. 93(10):4845-4850)

In addition, fMTX has been used to detect reconstitution of split dihydrofolate reductase ("DHFR") in protein complementation assays (Subramaniam et al., 2001, Nature Biotechnol. 19(8):769-772; Remy and Michnick, 1999, Proc. Natl. Acad. Sci. U.S.A. 96:5394-5399). In these assays, one fragment of DHFR is fused to a first protein, and the complementary fragment is fused to a second protein; binding between the proteins results in reconstitution of DHFR, measurable by binding to fMTX.

In another example of the use of small fluorescent probes in living cells, Farinas and Verkman (1999, J. Cell Biol. 274: 7603-7606) used cDNA transfection to target a single-chain antibody to a specified site such as an oranelle lumen. The single chain antibodies were fused to membrane targeting sequences. The targeted antibody functioned as a high affinity receptor to trap cell-permeable hapten-fluorophore conjugates.

In addition to use as detectors of protein complementation, small molecule ligands have been used to promote protein/protein interactions. Two different ligands can be joined and used to bring their binding partners into proximity—such compounds are referred to as "chemical inducers of dimerization" (Lin et al., 2000, J. Am. Chem. Soc. 122:4247-4248, citing Spencer et al., 1993, Science 262:1019-1024; Farrar et al., 1996, Nature 383:178-181; Belshaw et al., 1996, Proc. Natl. Acad. Sci. U.S.A. 93:4604-4607; Diver et al., 1997, J. Am. Chem. Soc. 119:5106-5109; Amara et al., 1997, Proc. Natl. Acad. Sci. U.S.A. 94:10618-10623; Clackson et al., 1998, Proc. Natl. Acad. Sci. U.S.A. 95:10437-10442).

3. SUMMARY OF THE INVENTION

The present invention relates to methods and compositions for detecting the location and/or function of a target molecule whereby the target molecule is linked, directly or indirectly via a detector molecule, to a labeled ligand.

By providing a means for monitoring target molecules in living cells, the present invention provides an adjunct or alternative to similar reporter functions provided by luciferase or Green Fluorescent Protein. Because a variety of compounds, including fluorescent compounds with diverse excitation/emission characteristics, can be linked to the ligands of the invention, the nature of the reporter signal is essentially uncoupled from the molecular structure of the detector molecule.

Thus, for example, the invention provides for methods and compositions which can be used in combination with Green Fluorescent Protein technology in which the ligand of the detector molecule/ligand pair is coupled to a red fluorophore. In another example, the same ligand linked to different fluorophores may be introduced under different conditions (e.g., time, temperature, pH, ion concentration) in the same experiment, to obtain information regarding the impact of changing conditions on the target molecule.

Further embodiments of the invention provide for naturally occurring or synthetic variant detector molecule/labeled ligand pairs in which the ligand has decreased affinity for any endogenous counterpart of the detector molecule. Such variants decrease or eliminate background signal and, in certain embodiments, circumvent issues raised by biological effects (such as toxicity, chemokine activity, etc.) produced by unmodified ligand/detector molecule interactions.

4. BRIEF DESCRIPTION OF THE FIGURES

FIG. 1A-F. A. Murine DHFR amino acid sequence (SEQ ID NO:4). B. Human DHFR amino acid sequence (SEQ ID NO:5). C. *Mycobacterium avium* DHFR amino acid sequence (SEQ ID NO:6). D. *Drosophila melanogaster* DHFR amino acid sequence (SEQ ID NO:7). E. *Escherichia coli* DHFR amino acid sequence (SEQ ID NO:8). F. *Plasmodium falciparum* DHFR amino acid sequence (SEQ ID NO:9).

FIG. 2. Table showing DMDP derivatives with modifications at the 5 position (R1) and substitutions on the phenyl group (R2 through R6) and varying selectivity of binding to *Mycobacterium avium* versus human DHFR (from Suling et al., 2000, Antimicrob. Agents Chemother. 44:2784-2793). The *M. avium*-selective derivatives may be detectably labeled and used according to the invention.

Figure 3B:
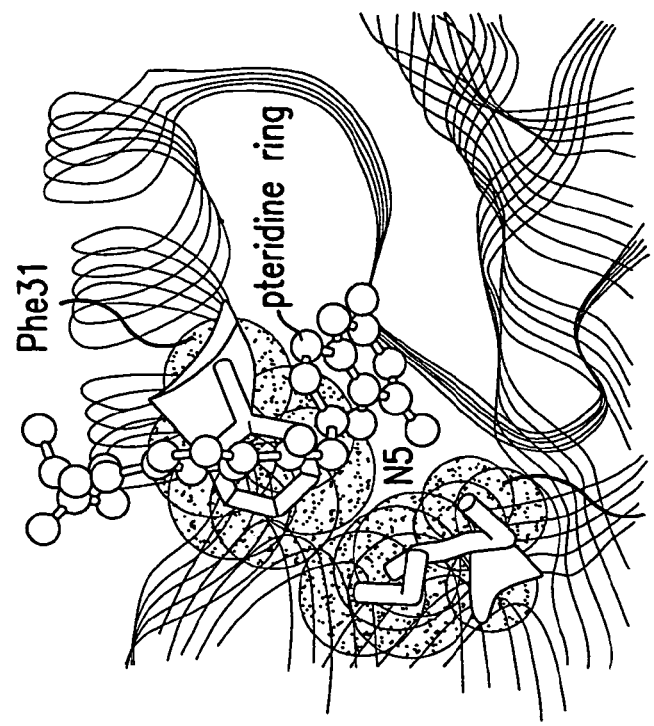
Figure 3A:
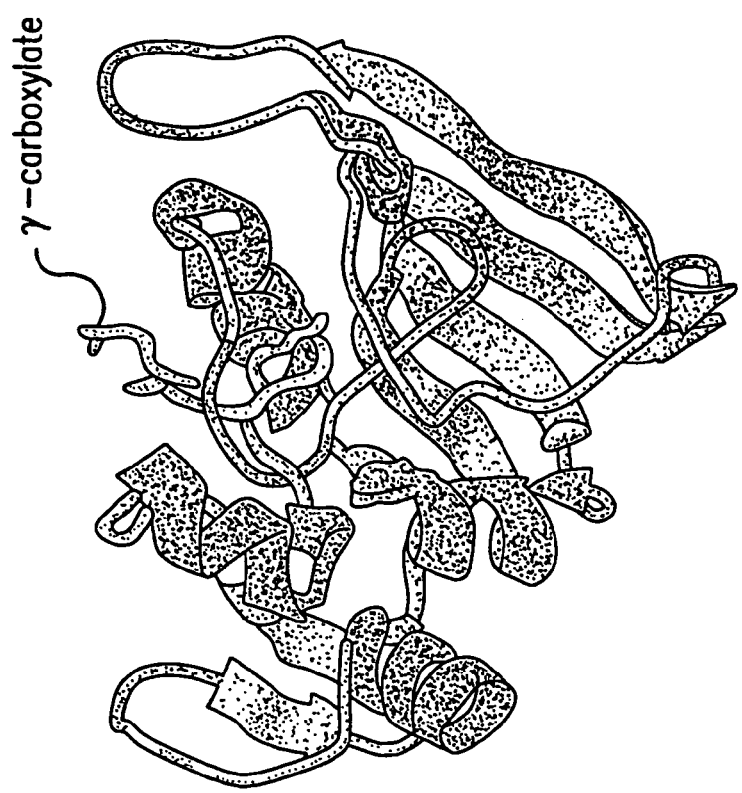

FIG. 3A-B. Three-dimensional structure of *Escherichia coli* DHFR complexed with methotrexate. The gamma-carboxylate group is easily accessible for modification. B. DHFR-methotrexate binding site highlighting hydrophobic interactions between the N5 position of the pteridine ring and residues Ile94 and Phe31. Drawings were prepared using the program RasMol.

Figure 4:
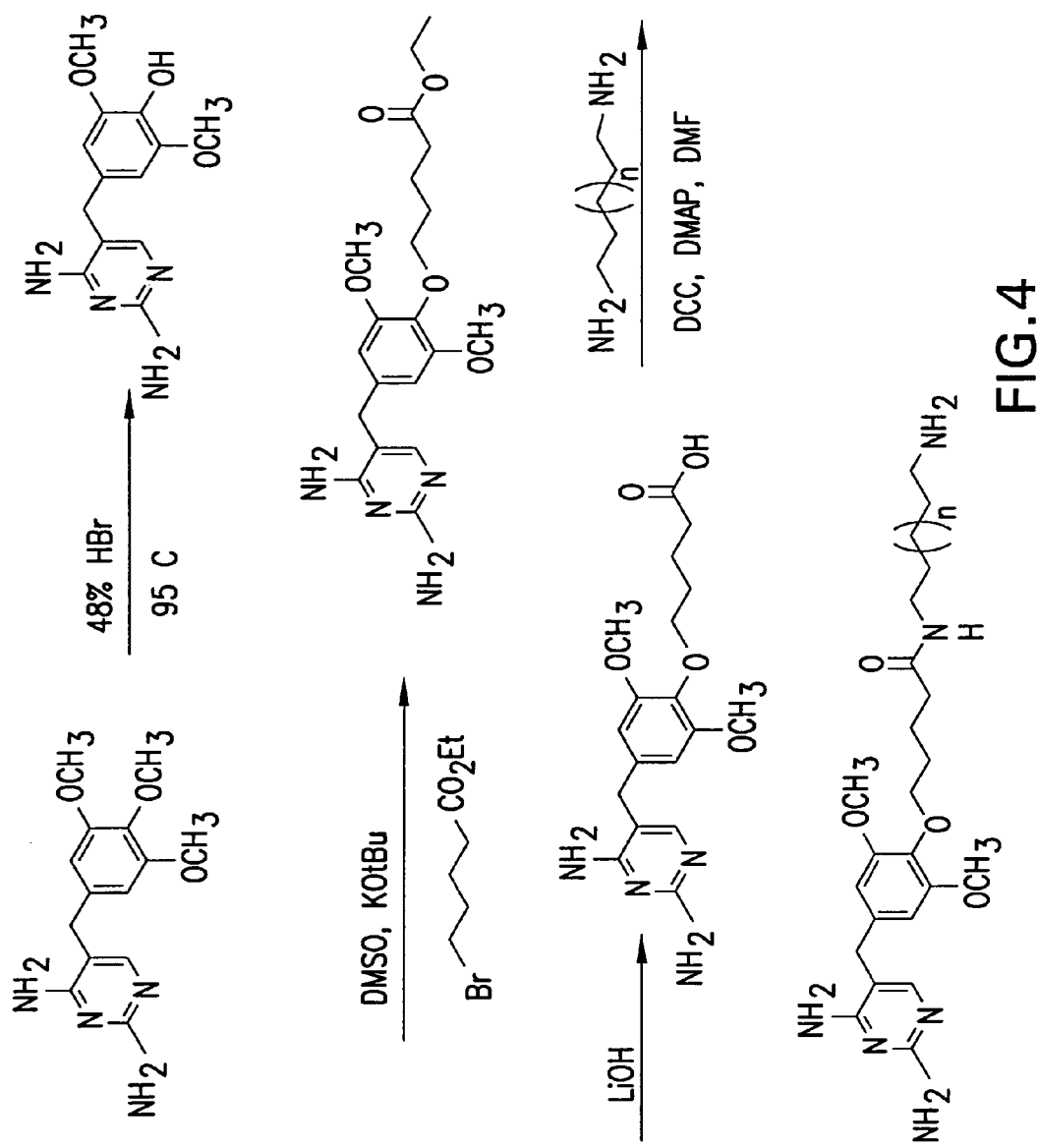

FIG. 4. Synthetic scheme for producing a 4'-alkylamino-substituted trimethoprim that may be conjugated to an amine-reactive detectable label.

FIG. 5A-B. A. Methotrexate. B. 5-alkyl-5-deazamethotrexate analogue of methotrexate. A label may be attached to the gamma carboxylic acid group.

5. DETAILED DESCRIPTION OF THE INVENTION

The present invention relates to methods and compositions for detecting a target molecule whereby the target molecule is linked, directly or indirectly, via a detector molecule, to a labeled ligand. For purposes of clarity, and not by way of limitation, the detailed description of the invention is divided into the following subsections:

1) target molecules;
2) detector molecule/ligand pairs; and
3) methods of use.

5.1 Target Molecules

The term "target molecule" is defined herein as a molecule of interest. The interest may be due to a role that the target molecule plays in an important biological process, such as cell proliferation, carcinogenesis, migration, metastasis, differentiation, or apoptosis. Alternatively, the interest may derive from a desire to study the expression and/or function of the molecule. For example, the target molecule may interact with other molecules in a biochemical pathway that researchers are attempting to define.

The target molecule may in addition or alternatively be of interest because its expression and/or function may be altered in the context of an assay system used to identify agents that alter the expression and/or function of the target molecule. For example, an assay may be used to identify agents, useful in medicine or industry, that modulate the expression of a target molecule, that alter the subcellular localization of a target molecule, or that increase or decrease activity of a target molecule. The cell in which the target molecule resides is referred to herein as the "host cell."

The target molecule may be any naturally occurring or synthetic molecule. For example, it may be a protein (including but not limited to a glycoprotein, a phosphoprotein, or a lipoprotein, with or without enzymatic activity, and may be an antibody or portion thereof), may be a nucleic acid, may be a lipid, may be a cofactor, and so forth. The target molecule does not consist essentially of an expression or localization accessory control element shared between numerous diverse molecular species, such as a signal or secretory peptide, membrane targeting sequence, nuclear localization signal, Shine-Delgarno sequence, poly-A sequence, TATA box, or CAAT box, for example. Where the target molecule is a nucleic acid, it may be a promoter element, a telomeric nucleic acid, a mRNA, or a rRNA, or an antisense RNA, to name a few among the various possibilities.

The target molecule may occur at the cell surface and may have at least a portion in contact with the extracellular space. Alternatively, the target molecule may be intracellular. The target molecule may, in non-limiting embodiments, have a portion which is, in vivo, embedded in a membrane.

A few specific, non-limiting examples of suitable target proteins include proteins in the Ras family, proteins involved in apoptosis, kinases, calmodulin, and membrane-specific proteins. However, virtually any molecule of interest may be used as a target molecule provided it is within the definition provided above.

A target molecule of the invention may be linked, directly or indirectly, to a detector molecule. A direct linkage is structural. An indirect linkage may be structural or functional. Structural linkages may be covalent or non-covalent. Non-limiting examples of functional linkages would include a target promoter that controls the transcription of a mRNA that is translated to produce a detector protein, a target protein which binds to a promoter element and thereby modulates expression of a detector protein; and a target molecule which activates a kinase molecule that in turn activates a detector protein by enabling it to bind to its ligand.

In preferred non-limiting embodiments, the target and detector molecules are both proteins and the target protein and the detector protein are both comprised in a fusion protein (a direct linkage). Preferably, the linkage between the target protein and the detector protein in the fusion protein does not substantially functionally alter either component, so that neither the normal biological activity of the target molecule nor the affinity of the detector protein for its ligand are substantially disrupted.

In further non-limiting embodiments, a target molecule may be a nucleic acid, linked to a detector molecule which may be either a nucleic acid or a protein. For example, a target promoter element may be operatively linked to a nucleic acid that is transcribed to produce a detector mRNA (an indirect functional linkage). Similarly, a target promoter may be operatively linked to a nucleic acid encoding a detector protein (also an indirect functional linkage). In other exemplary embodiments, a target mRNA may be co-transcribed with a detector mRNA (a direct linkage). Alternatively, a target mRNA may be linked to a detector protein either via an aptameric relationship or via an intermediary aptameric nucleic acid that comprises a region complementary to the target mRNA and a region that has affinity for the detector protein (an indirect structural mediator). The terms "aptamer" and "aptameric" as used herein refer to the ability of certain nucleic acid molecules to bind to non-nucleic acid molecules.

5.2 Detector Molecule/Ligand Pairs

A "detector molecule", as defined herein, is a molecule that can be linked to both a target molecule as well as a ligand. As set forth in the preceding section, an indirect linkage between a detector molecule and a target molecule may be either structural or functional. The linkage of ligand to detector molecule is always structural (although it may be direct or indirect) and is specific; structural aspects of each promote binding of one to the other. Specificity notwithstanding, the ligand may be capable of binding different detector molecules, and the detector molecule may be capable of binding a number of different ligands. As an example, a glucocorticoid receptor molecule, as a detector protein, can bind to a variety of ligand steroid molecules, including agonists such as dexamethasone as well as antagonists such as RU-486; in each case binding is specific but different ligands can bind to the same receptor.

A detector molecule may belong to any chemical class of molecule, provided that it can be directly or indirectly linked to a target molecule and can bind to a ligand (as defined below).

In preferred embodiments, the detector molecule is a protein. Protein subclasses suitable as detector proteins include but are not limited to enzymes, DNA binding proteins, receptors, antibodies and cytostructural proteins. In other, non-limiting embodiments of the invention, the detector molecule may be a nucleic acid. In still other non-limiting embodiments, the detector molecule may be a carbohydrate, a lipid, or a cofactor molecule.

In one series of specific embodiments, the detector molecule may be a mRNA that can be transcribed in series with a target mRNA, and may then bind to a ligand which is a labeled nucleic acid molecule having at least a portion that is complementary to the detector mRNA and capable of hybridizably binding to it in the host cell. In another series of specific embodiments, the detector molecule may be a nucleic acid that aptamerically binds to the target molecule; examples of nucleic acids that bind to prion protein (Weiss et al., 1997, J. Virol. 71(11):8790-8797) or to thrombin (Block et al., 1992, Nature 355:564-566) are known. In yet another series of specific embodiments, detector RNA molecules that bind to particular target entities may be identified by Systematic Evolution of Ligands by eXponential amplification ("SELEX; Wilson and Szostak, 1999, Annu. Rev. Biochem. 68:611-647); "evolved" RNAs that bind to arginine, ATP, citrulline, HIV-1 rev peptide, have been identified in this manner. Ligands that bind to such detector aptamers or "evolved" RNAs may be labeled nucleic acids comprising complementary regions or other suitable binding partners.

The detector molecule may be modified to facilitate its intracellular localization. For example, where the detector molecule is a protein, it may be modified to include a membrane targeting signal, such as, but not limited to, a peptide such as GCVQCKDKEA (SEQ ID NO:1), GCIKSKENKS (SEQ ID NO:2) or GCTLSAEERA (SEQ ID NO:3) may be appended to the amino terminus of the detector protein.

The term "ligand", as defined herein, encompasses, but is not limited to, molecules that bind to receptors (e.g. a steroid compound binds to a glucocorticoid receptor), molecules that bind to specific targets (e.g., a DNA molecule having a particular sequence which binds to a DNA binding protein), cofactors (e.g., heme for binding to hemoglobin or a subunit thereof), functional inhibitors, and substrates (e.g., clavulinate is a suicide substrate for beta-lactamases in penicillin-resistant bacteria). Further specific examples of potential ligands include but are not limited to aptamers or SELEX "evolved" RNAs (see above) which bind to a partner detector molecule linked to a target molecule. Referring to a molecule as a "ligand" relative to its binding partner does not mean that it is smaller than its binding partner, but to facilitate host cell entry and transport smaller molecules are preferred. In preferred, non-limiting embodiments, the ligand is a small molecule having a molecular size of 500-2000 daltons.

Any suitable label known in the art may be used. Non-limiting examples of fluorescent labels include fluorescein, tetramethylrhodamine, Amplex-Red, coumarin, rose bengal, Texas red and Bodipy® fluorophores. Non-limiting examples of chromogenic labels include BCIP (5-bromo-4-chloro-3-indoyl phosphate), a substrate of alkaline phosphatase, which is used in conjunction with nitro blue tetrazolium and X-Gal (5-bromo-4-chloro-3-indoyl B-D galactopyranoside), a substrate of B-Galactosidase.

In specific non-limiting embodiments, a detector molecule is a protein detectable by FlAsH, a technique in which the sequence Cys-Cys-Xaa-Xaa-Cys-Cys (SEQ ID NO:10) (where Xaa is an noncysteine amino acid) is genetically fused to or inserted within the protein, where it can be specifically recognized by a membrane-permeant fluorescein derivative ligand with two As(III) substituents, "FlAsH", which fluoresces only after the arsenics bind to the cysteine thiols (Adams et al., 2002, J. Am. Chem. Soc. 124(21):6063-6076; Griffin et al., 2000, Methods Enzymol. 327: 565-578; Griffin et al., 1998, Science 281: 269-272). In related embodiments, ReAsH or other analogous biarsenical compounds may be used.

The choice of a detector molecule/ligand pair to label a target molecule may be influenced by a variety of factors. First, as discussed in the preceding section, when the target molecule is directly linked to the detector molecule the functionality of both should not be substantially affected. Second, the target molecule/detector molecule should be accessible to ligand; for example, where the target molecule/detector molecule reside in the cytoplasm the ligand must be able to penetrate the cytoplasmic membrane; where the target molecule/detector molecule reside in the endoplasmic reticulum the ligand must be able to enter the endoplasmic reticulum, etc. Third, where there is a particular label that is desirable to attach to the ligand (for example, a fluorescent compound to be used as an adjunct to GFP), ability of the labeled ligand to bind to the detector molecule should not be substantially decreased by, for example, steric hindrance or electrostatic interactions. Fourth, depending on the duration and nature of labeling of molecular target/detector molecule to labeled ligand, the potential effect of the labeled ligand on the host cell should be considered; for example, the labeled ligand may be toxic to the host cell at certain concentrations and after a certain period of time. Fifth, in a related concern, biological activity of the detector molecule may perturb the function or viability of the host cell, particularly if a threshold amount of the molecule is exceeded, so that if the molecular target is to be produced at high concentrations, a detector molecule should be chosen which can be present at such concentrations without being toxic. Sixth, if the detector molecule has an endogenous counterpart in the host cell, it may be desirable to reduce signal from binding of labeled ligand to endogenous molecule, for example, by using a ligand and/or detector molecule with distinctive structure(s) so that binding to detector molecule is favored. Other factors to be considered would be apparent to the person skilled in the art.

Regarding the effects of ligand or detector molecule on the host cell and/or the reduction of background signal resulting from binding of labeled ligand to an endogenous counterpart of the detector molecule, the present invention provides for natural or synthetic variants of ligands and detector molecules endogenous to a host cell which avoid these problems. The term "variant" as used herein considers the detector molecule or its ligand relative to an endogenous counterpart in the host cell; a naturally-occurring E. coli DHFR detector protein in a mammalian cell would be considered a variant. A mutant of the endogenous mammalian DHFR of the host cell or a mutant of the E. coli DHFR would also be considered to be "variants".

To avoid ligand toxicity, the ligand may be selected or may be structurally modified to disfavor its binding to any endogenous counterpart of the detector molecule. Most preferably, the ligand may be selected or modified to have a high affinity for the detector molecule and a low affinity for its endogenous counterpart, where binding to the detector molecule has little if any biological effect. In one non-limiting example where the detector protein is an enzyme, the labeled ligand may be a suicide substrate for the detector protein without substantially binding to and/or without inactivating significant amounts of a corresponding endogenous enzyme.

In particular non-limiting embodiments of the invention, both a ligand and a detector molecule are selected or modified to improve the specificity of binding and, in certain instances, to avoid undesirable activities of the ligand and/or detector molecule. A number of detector molecules originating in organisms evolutionarily distant from the host cell and naturally occurring detector molecule variants may be available, as may be ligands which selectively bind such detector molecules. Further, methods of redesigning interfaces between ligands and their binding partners are known in the art (see, for example, Clackson et al, 1998, Proc. Natl. Acad. Sci. U.S.A. 95:10437-10442; Clackson, 1998, Curr. Opin. Structural Biol. 8:451-458).

In additional embodiments of the invention, the ligand may be structurally modified to improve its access to or retention in a desired cellular location. For example, its ability to cross a cell membrane may be improved by attaching a lipophilic portion (for example, via an ester linkage that could be cleaved inside the cell) or by "piggy-backing" the ligand on a second molecule. Ligand (modified or unmodified) may be incorporated into a microparticle which is taken up by a cell via a clathrin-coated vesicle or other uptake mechanism, uptake may be facilitated by a permeabilizing agent such as dimethylsulfoxide, or ligand export mechanisms may be inhibited.

The following are non-limiting examples of detector protein/ligand pairs that may be used according to the invention: DHFR/antifolate; glucocoritcoid receptor/steroid (or glucocorticoid receptor/agonist or glucocorticoid receptor/antagonist); TET-repressor/tetracycline; penicillin binding proteins/penicillin or cephalosporin (fluorescently labeled penicillins are commercially available, such as BOCILLIN FL and BOCILLIN 650/665 (Molecular Probes, Inc., Oregon)); acetylcholinesterase/acetylcholine (fluorescently labeled acetylcholine is commercially available, such as Amplex Red acetylcholine (Molecular Probes Inc., Oregon)); carboxypeptidase A/MTX; cyclophilin prolyl isomerase/cyclosporin; FK506-binding protein (FKBP)/FK506 and rapamycin; beta-lactamase/clavulinate; DNA binding site/DNA binding protein; and hemoglobin/heme. For cyclophilin prolyl isomerase/cyclosporin and FK506-binding protein (FKBP)/FK506 and rapamycin, strategies for redesigning ligand/protein interfaces and modified structures are set forth in Clackson, 1998, Curr. Opin. Struct. Biol. 8:451-458.

In preferred non-limiting embodiments of the invention, the detector protein is DHFR. DHFR is an enzyme involved in de novo synthesis of purines and pyrimidines, the building blocks of nucleic acids. DHFR adds two hydrogens to dihydrofolic acid, producing tetrahydrofolic acid. Methotrexate ("MTX") tightly binds to the active site of the enzyme, thereby inhibiting nucleotide biosynthesis. The anti-proliferative toxic effect of MTX is particularly apparent in rapidly dividing cells, making MTX useful as a chemotherapeutic agent. Regarding the toxicity of MTX, DNA damage has been observed to occur in human cells at an extracellular concentration of 10 micromolar, the toxicity in human leukocytes observed at 2 micromolar.

The present invention provides for the use of DHFR as a detector protein which may be directly or indirectly linked to a molecular target. In preferred, non-limiting embodiments of the invention, DHFR (or a portion thereof comprising the active site) and a protein molecular target are both comprised in a fusion protein. DHFR or a portion thereof may be positioned at the amino or carboxy-terminus of the target protein; one orientation may be preferred to preserve the functional characteristics of the proteins. At least the active site of DHFR is comprised in the fusion protein, to allow for binding of labeled MTX or an MTX analog. DHFR may be of human or non-human origin. Non-limiting examples of DHFR proteins that may be used according to the invention include proteins as described in Chang et al., 1978, Nature 275:617-624 (*Mus musculus* DHFR, GenBank Acc. No. NM 010049: FIG. 1A); Morandi et al., J. Mol. Biol. 156: 583-607 (*Homo sapiens* DHFR, GenBank Acc. No. NM 000791; FIG. 1B); Hao et al., 1994, J. Biol. Chem. 269(21):15179-85 (*Drosophila* DHFR, GenBank Acc. No. U06861; FIG. 1D); Fling and Richards, 1983, Nucl. Acids Res. 11:5147-5158 (*Escherichia coli* DHFR; GenBank Acc. No. X00926; FIG. 1E).

MTX can be chemically modified without disrupting receptor binding by adding modifications at the γ-carboxylate position (see FIG. 3A; Benkovic et al., 1988, Science 239: 1105-1110; Bolin et al., 1982, J. Biol. Chem. 257:13650-13662). Accordingly, MTX may be chemically linked to a wide variety of fluorophores or chormophores. Indeed, a number of methotrexate-conjugated fluorophores are commercially available from Molecular Probes (Eugene, Oreg.). These include fluorescein-methotrexate, Texas Red™-methotrexate, BODIPY™-methotrexate, and AlexaFluor™-methotrexate. References describing fluorescently labeled MTX include Gapski et al., 1975, J. Med. Chem. 18:526-528; Fan et al., 1991, Biochem. 30(18):4573-4580 and Rosowsky et al., 1982, J. Biol. Chem. 257(23):14162-14167.

Several approaches may be used in order to avoid the toxic effects of MTX on host cells. The specific DHFR detector protein may be selected such that a labeled ligand favors binding to the detector protein rather than endogenous DHFR.

In one series of embodiments, a naturally occurring DHFR from a species other than that of the intended host cells may be used which binds to substrates that do not have high affinity for endogenous DHFR. For example, DHFR from *E. coli* may be used as a detector protein, and labeled trimethoprim, which favors binding to the bacterial DHFR over its mammalian counterpart, may be used as ligand. Trimethoprim (2,4-Diamino-5-(3,4,5-trimethoxybenzyl)pyrimidine) binds tightly to the *E. coli* form of Dihydrofolate Reductase (KI=ca. 1 nm). However, trimethoprim's affinity for mammalian forms of DHFR is over 1000-fold lower (KI=ca. 3700 nm; Baccanari et al., 1982, Biochemistry 21: 5068-5075). This selectivity for the *E. coli* form of DHFR is advantageous for the labeling and detecting of proteins in mammalian cells. Trimethoprim that has been functionalized with a fluorescent or otherwise detectable label may be used to selectively bind to an *E. coli* DHFR fusion protein expressed in mammalian cells without binding appreciably to endogenous DHFR. This is important to minimize background. Thus, trimethoprim and *E. coli* DHFR comprise an orthogonal ligand-receptor pair for the purposes of labeling and detecting fusion proteins in all mammalian cell types.

In specific, non-limiting embodiments of the invention, labeled trimethoprim may be prepared which is substituted at the 4' position. 4'-substituted trimethoprim retains nanomolar affinity for *E. coli* DHFR as well as selectivity over mammalian forms of DHFR if the substituent is attached via an alkyl linker with a chain length longer than 3 carbons (Roth et al., 1981, J. Med. Chem. 24: 933-941; Kuyper et al., 1985, J. Med. Chem. 28: 303-311). 4'-alkylamino-substituted trimethoprim may be prepared as follows (and see FIG. 4). Trimethoprim may be selectively demethylated at the 4' position according to the method of Brossi et al., 1971, J. Med. Chem. 14: 58-59. The resulting phenol compound may be alkylated via reaction with a bromo-alkanoate ester (Kuyper et. al., 1985, J. Med. Chem. 28: 303-311). The ester may then be hydrolyzed and reacted with a diamino alkane of desired length using a carbodiimide, or other peptide coupling reagent. The product, a 4'-alkylamino-substituted trimethoprim may then be easily linked to commercially available, amine-reactive fluorescent molecules (e.g., Texas Red®-X succimidyl ester, fluorescein succimidyl ester, malachite green isothiocyanate; all available from Molecular Probes, Eugene, Oreg.).

As regards related embodiments, Li et al., 2000, J. Mol. Biol. 295(2): 307-323 have determined that DHFR from *Mycobacterium tuberculosis* differs from human DHFR in relevant residues around the active site. Specifically, the *M. tuberculosis* enzyme residues Ala101 and Leu102 near the N6 of NADP are distinctly more hydrophobic than human DHFR, and, in a region near atoms N1 and N8 of methotrexate, *M. tuberculosis* DHFR has a "pocket" that can bind a glycerol molecule, whereas this same region is essentially filled with hydrophobic side-chains in the human enzyme. The present invention provides for the use of *M. tuberculosis* DHFR (or an active portion thereof) as a detector protein and, as ligand, detectably labeled MTX modified to fit in the *M. tuberculosis* DHFR active site, but not in the active site of endogenous enzyme (e.g., human DHFR).

In a related embodiment, DHFR (or a portion thereof) from *Mycobacterium avium* may be used as detector protein and labeled 2,4-diamino-5-[(2-methoxy-4-carboxybutyloxy) benzyl]pyrimidine may be used as a ligand, which has been found to selectively bind to *Mycobacterium avium* DHFR (Rosowsky et al., 2002, J. Med. Chem. 45(1):233-241). Alternative ligands which may be labeled according to the invention are described in Debnath, 2002, J. Med. Chem. 45(1): 41-53 (2,4-diamino-5-deazapteridine derivatives), Suling and Maddry, 2001, J. Antimicrob. Chemother. 47(4):451-454 (1-deaza-7,8-dihydropteridine derivatives); Suling et al., 2000, Antimicrob. Agents Chemother. 44:2784-2793 (2,4-diamino-5-deazapteridine derivatives; see FIG. 2). The cloning of *M. avium* DHFR was reported in Zwyno-vanGinkel, 1997, FEMS Microbiol. Letts. 156:69-78, and the sequence is available as GenBank Acc. No. AF006616 (FIG. 1C).

Similar approaches using a naturally occurring DHFR gene may utilize the DHFR of a malarial parasite( e.g., of *Plasmodium falciparum*, Bzik et al., 1987, Proc. Natl. Acad. Sci. U.S.A. 84(23):8360-8364; GenBank Acc. No. J03028, FIG. 1F), the DHFR of *Toxoplasma gondii* (Roos, 1993, J. Biol. Chem. 268(9):6269-6280; GenBank Acc. No. L08489), the DHFR of *Pneumocystis carinii* (Edman et al., 1989, Proc. Natl. Acad. Sci. U.S.A. 86(22): 8625-8629; GenBank Acc. No. M26495 and M26496); and the DHFR-thymidilate synthase gene of *Trypanosoma cruzi* (Reche et al., 1994, Mol. Biochem. Parasitol.65(2):247-258; GenBank Acc. No. L22484), and so forth. In this regard, compounds used as selective anti-folate agents against diseases caused by pathogenic protozoans may be labeled and used according to the invention in conjunction with protozoan DHFRs as detector proteins. Examples of such compounds include but are not limited to pyrimethamine and its analogs (see Chan et al., 2002, Bioorg. Med. Chem. 10(9):3001-3010), compounds described in Gilbert, 2002, Biochim Biophys Acta 1587(2-3):249-57, phenoxypropoxybiguanides (Jensen et al., 2001, J. Med. Chem. 44(23):3925-3931), diaminopyrimidine derivatives (Lau et al., 2001, Antimicrob. Agents Chemother. 45(1):187-95), piritrexim, trimethoprim, proguanil, cycloguanil and trimetrexate (see Hitchings, 1988, Nobel Lecture). If the DHFR gene is antifolate resistant, further modifications of the ligand may be made.

In additional embodiments of the invention, a DHFR may be structurally modified to alter its substrate binding characteristics and thereby confer desired selectivity and/or binding affinity.

In one set of non-limiting embodiments, A "bump-hole" strategy may be used to alter the methotrexate-binding site of DHFR (Clackson, 1998, Curr. Opin. Struct. Biol. 8:451-458; Clackson et al., 1998, Proc. Natl. Acad. Sci. U.S.A. 95:10437-10442). Mutagenesis may be employed to increase the size of the methotrexate-binding site of DHFR (the "hole"). A complementary modification may be added to methotrexate (the "bump"). The bumped methotrexate should bind weakly to wild-type DHFR, but it should interact specifically with the mutant.

In a particular non-limiting embodiment, modification may be performed as follows. The methotrexate binding site of *E. coli* DHFR is shown in FIG. 3B. The pteridine ring of methotrexate aids binding to DHFR through both hydrophilic and hydrophobic interactions. The N5 position of the pteridine ring has no associated hydrogen bonds, rather it contributes to binding solely through hydrophobic interactions with residues Ile94 and Phe31. An alkyl group added at the N5 position would lower the binding affinity to wild-type DHFR. Examples of alkyl substituents include propyl, butyl, and phenyl substituents and derivatives thereof that retain the carbon backbone. A complementary mutation of Ile94 to Ala94 would increase the size of the binding pocket, thus accommodating the modified methotrexate. This mutation could be effected without disrupting the structure of the protein itself.

5-alkyl-5-deazamethotrexates (see FIG. 5 for structure) have been synthesized as antifolate drug candidates. The inhibitory effect on DHFR of 5-butyl-5-deazamethotrexate was lowered relative to MTX by 17-fold (Piper et al., 1995, J. Heterocycl. Chem. 32:1205-1212). The synthesis method for these methotrexate analogues has been published (Piper et al., 1995, J. Heterocycl. Chem. 32:1205-1212; Piper et al., 1997, J. Med. Chem. 40:377-384). Standard subcloning may be used change the Ile94 residue of *E. coli* DHFR to Ala94. The mutant DHFR may be purified, and a stopped-flow competitive inhibitor assay may be used to determine the binding affinity of 5-butyl-5-deazomethotrexate to both wild-type and mutant DHFR (Appleman et al., 1988, J. Biol. Chem. 263: 10304-10313)

Another example of a "bump-hole" modification is substitution of a phenyl group at the N5 position, which may be used to lower the binding affinity to wild-type DHFR even more than a butyl substitution. A combination of mutations to DHFR may be made to accommodate the phenyl group.

Further, various mutations are known which result in MTX resistance. These include, but are not limited to, substitutions in human DHFR at position 22 (leucine) to arginine or phenylalanine and at position 31 (phenylalanine) to serine or tryptophan (Banerjee et al., 1994, Gene 139(2): 269-274; Morris and McIvor, 1994, Biochem. Biopharmacol. 47(7): 1207-1220; Simonsend and Levinson, 1983, Proc. Natl. Acad. Sci. U.S.A. 80(9):2495-2499). MTX may be modified to bind to the active site in DHFR natural or synthetic variants that do not bind unmodified MTX with sufficient affinity.

Where DHFR is the detector protein, the extracellular concentration of ligand may be between 1 nanomolar and 100 micromolar. In preferred non-limiting embodiments, the concentration is between 0.1 and 10 micromolar. For uses in which a host cell is exposed to labeled ligand for a prolonged period of time, it is desirable to use a dose which will not result in significant toxicity; for example but not by way of limitation, less than 10 micromolar or preferably less than 2 micromolar.

5.3 Methods of Use

The detector molecule/labeled ligand systems of the invention can be used to detect the presence, location and functionality of molecular targets in the context of living cells.

Reporters of Protein Location

In preferred embodiments of the invention, the present invention provides for methods of localizing and following a target protein fused to a detector protein.

For example, in a set of non-limiting embodiments, a nucleic acid construct may be produced which encodes a protein target fused (at its amino terminus or carboxy terminus) to a detector protein. The fusion construct may be operatively linked to a promoter which may be, depending on experimental design, the naturally occurring promoter of the target protein (a "target homologous promoter") or a heterologous promoter. The promoter/fusion construct may then be introduced into a host cell using standard techniques (e.g., via a viral vector, transfection, etc.). The host cell may then be cultured under conditions consistent with the experimental design. Detectably labeled ligand is introduced into the host cell. The detectably labeled ligand may be introduced into the host cell during the culture period or in one or more separate step(s), including prior to the start of culture or after culture. In preferred non-limiting embodiments of the invention, the host cell is exposed to labeled ligand at a non-toxic concentration and/or for a period of time which will minimize toxicity. Then, labeled ligand bound to detector protein may be detected using standard techniques. For example, where the ligand carries a fluorescent label, the location of labeled ligand bound to detector protein (and hence the location of target protein) may be detected using fluorescence microscopy.

In preferred, non-limiting examples of the invention, the detector protein may be a DHFR and the ligand may be an antifolate compound. Preferably, the detector protein DHFR is structurally distinct from a DHFR endogenous to a host cell, and the ligand is selected to preferentially bind to the detector protein DHFR rather than to endogenous DHFR. Various structural distinctions of DHFR and its ligands are set forth above.

In view of the diversity of labels that can be linked to ligands according to the invention, the ability to concurrently study the fates and locations of different target proteins is substantially expanded relative to what has been available. For example, a plurality of target proteins can each be fused to different detector proteins, each of which binds to a distinctively labeled ligand. Similarly, one or more target/detector protein fusions can be used in conjunction with currently available reporters, such a target protein fused to GFP.

Since the same ligand can be linked to different labels, the result of introduction of ligand under varying conditions can be evaluated. For example, a host cell containing a target/detector protein fusion construct can be cultured under a first set of conditions, and exposed to ligand linked to label "A". Subsequently, culture conditions can be changed and the cell can then be exposed to ligand linked to label "B". The effect of changing conditions may be determined by comparing the amount and location of labels A and B bound to the target/detector fusion protein.

In alternative embodiments of the invention, the detector molecule may be a RNA molecule, for example a RNA molecule (e.g., identified by the SELEX technique) which specifically binds to a target protein. A nucleic acid molecule comprising a nucleic acid which may be transcribed to produce the detector RNA, operatively linked to a suitable promoter element, may be introduced into a host cell using standard techniques (for example, by transfection, via a viral vector, etc.). Transcribed detector RNA may then encounter and bind to the target protein in the nucleus or cytoplasm (including a subcellular compartment thereof). An appropriate ligand may be either a labeled second RNA or a DNA molecule which is complementary to at least a portion of the detector RNA such that they may hybridizably bind in the host cell. The ligand nucleic acid may be either transcribed in the host cell (e.g., in the presence of one or more labeled NTP, where for example the ligand RNA may be designed to contain a higher than average proportion of labeled nucleotide(s)) or may be synthesized and labeled outside the host cell and introduced by standard techniques.

Reporters of RNA Location

The present invention may also be used to determine the location of a target RNA, which may be useful, for example, in studying the transport of a target RNA from the nucleus to the cytoplasm, or for studying the presence of a target RNA in polysomes.

In particular embodiments, the invention provides for methods of detecting a target RNA in a host cell, comprising preparing a nucleic acid construct comprising a promoter element operatively linked to a nucleic acid that is transcribed to produce the target RNA linked to a detector RNA molecule (a "fusion RNA"), introducing the nucleic acid construct into a host cell by standard techniques (e.g., by transfection, via a viral vector, etc.), culturing the host cell under conditions such that a target RNA/detector RNA fusion RNA is produced; introducing, into the host cell, an effective (to provide detection) concentration of a detectably labeled ligand of the detector RNA; and then detecting the presence of the target RNA by detecting labeled ligand bound to the fusion RNA. The labeled ligand may be a nucleic acid, at least a portion of which is complementary to the target RNA such that it hybridizably binds to the target RNA in the host cell. The ligand RNA may be introduced into the host cell either by synthesis in vivo in the host cell or by synthesis and introduction from outside the cell, e.g., by transfection or via a viral vector. Where the ligand is a nucleic acid that is synthesized in the host cell, it may be, for example, an RNA molecule designed to contain a high proportion of a certain nucleotide X and then transcribed in the presence of labeled XTP. Where the detector RNA is an aptamer, the labeled ligand may be a labeled protein, carbohydrate, lipid, etc.

Reporters of Protein Interaction

In another set of embodiments, the invention may be used to detect the interaction of target proteins. A first target protein may be fused to a first detector protein, and a second target protein may be fused to a second detector protein using nucleic acid constructs and methods as set forth above, such that they are both expressed in a host cell. If the ligands of the detector proteins carry different fluorophores, physical interaction of the proteins, by bringing the fluorophores into close proximity (e.g., with 100 angstroms) may result in fluorescence resonance energy transfer ("FRET"). Preferably, the first and second target proteins are bound to different detector proteins having different ligands, and the ligands are each labeled with a different fluorophore. Other experimental designs are envisaged: for example, the detector proteins may be the same but different ligands (e.g., an agonist and an antagonist) may be used, or the same ligand bound to different labels may be used provided that the differently labeled ligands are introduced into the cell sequentially and/or under different conditions. Alternatively, a target/detector fusion may be used in FRET studies with a second target bound to another fluorescent label, such as GFP, wherein binding of the first target to the second target results in FRET.

Reporters of Promoter Activity

In yet another set of embodiments, the invention may be used to measure activity of a promoter element of interest.

According to such embodiments, a nucleic acid comprising a sequence that encodes a detector protein may be operatively linked to a promoter element of interest (additional intervening sequences may be present) and the resulting construct may be introduced into a suitable host cell. The activity of the promoter may be monitored by determining the level of detector protein expressed; such activity may be measured by binding expressed detector protein to a labeled ligand.

Alternatively, the target promoter may be operatively linked to a nucleic acid that is transcribed to produce a detector RNA, and the amount of detector RNA produced may be determined by binding transcribed detector RNA to a labeled ligand, such as a labeled nucleic acid having at least a portion which is complementary to the detector RNA such that it hybridizably binds to the detector RNA in the host cell or, where the detector RNA is an aptamer, a labeled protein, lipid, or carbohydrate etc. having an affinity thereto.

Such embodiments may be useful in the context of assay systems to identify agents or conditions (e.g., pH, temperature, etc.) useful in medicine or industry, which increase or decrease promoter activity. In such assay systems, comparable host cells may be cultured in the presence and absence of a test agent or condition, and then the amount of detector RNA or protein produced may be compared.

Where the invention is used to measure promoter activity, it is desirable to distinguish between bound and unbound labeled ligand. This may be accomplished, for example, by selecting a ligand that irreversibly and stably binds to detector molecule but that is rapidly degraded in the unbound state. Alternatively, a ligand that changes cellular compartments upon binding to a detector molecule may be used (e.g., unbound ligand resides in the cytoplasm, bound ligand accumulates in the nucleus). If the viability of the cell need not be preserved, the detector molecule may simply be harvested and bound to labeled ligand in vitro.

In specific non-limiting embodiments, a promoter of interest may be operatively linked to a gene encoding a DHFR detector protein, and promoter activity may be measured by determining the amount of DHFR detector protein produced that binds to a detectably labeled antifolate agent such as methotrexate or an analogue thereof.

Various publications, including patents, patent applications, and non-patent publications are cited herein, which are hereby incorporated by reference in their entireties.

What is claimed is:

1. A method of detecting a target protein in a mammalian host cell, wherein the mammalian host cell expresses an endogenous functional dihydrofolate reductase gene, comprising: (a) preparing a nucleic acid construct comprising a promoter element operatively linked to a nucleic acid encoding the target protein and a nucleic acid encoding a bacterial dihydrofolate reductase; (b) introducing the nucleic acid construct into a host cell; (c) culturing the host cell under conditions such that a target protein/dihydrofolate reductase fusion protein is expressed; (d) introducing, into the host cell cultured according to step (c), a detectably labeled trimethoprim; and (e) detecting the presence of the target protein by detecting labeled trimethoprim bound to the fusion protein.

2. The method of claim 1, wherein the trimethoprim is fluorescently labeled.

3. The method of claim 2, wherein the presence of the target protein is detected by fluorescence microscopy.

* * * * *

UNITED STATES PATENT AND TRADEMARK OFFICE
CERTIFICATE OF CORRECTION

PATENT NO. : 7,575,866 B2  Page 1 of 1
APPLICATION NO. : 11/219506
DATED : August 18, 2009
INVENTOR(S) : Cornish et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this

Seventh Day of September, 2010

David J. Kappos
*Director of the United States Patent and Trademark Office*